United States Patent [19]
Gregory et al.

[11] 3,989,821
[45] Nov. 2, 1976

[54] POLYPEPTIDES

[75] Inventors: Harold Gregory; Peter Leslie Walton, both of Macclesfield, England

[73] Assignee: Imperial Chemical Industries Limited, London, England

[22] Filed: Apr. 30, 1975

[21] Appl. No.: 573,027

Related U.S. Application Data

[62] Division of Ser. No. 420,573, Nov. 30, 1973, Pat. No. 3,903,069.

[30] Foreign Application Priority Data
Dec. 18, 1972 United Kingdom............... 59742/72
Jan. 29, 1973 United Kingdom................. 4387/73

[52] U.S. Cl. .............................................. 424/178
[51] Int. Cl.$^2$........................................ A61K 37/26
[58] Field of Search..................................... 424/178

[56] References Cited
UNITED STATES PATENTS
3,364,116  1/1968  Bodanszky et al.................. 424/178

*Primary Examiner*—Frederick E. Waddell
*Attorney, Agent, or Firm*—Cushman, Darby & Cushman

[57] ABSTRACT

The modification of porcine or bovine insulin by treatment with a lysine specific amino-endopeptidase, which has the effect of removing L-lysyl-L-alanine from the B chain of the insulin. The products obtained have full insulin-like activity but are less antigenic.

6 Claims, No Drawings

POLYPEPTIDES

This is a division of application Ser. No. 420,573, filed Nov. 30, 1973, and now U.S. Pat. No. 3,903,069.

This invention relates to polypeptides and in particular it relates to polypeptides obtained by modification of porcine or bovine insulin.

It is well-known that administration of insulin is of immense value in the management of diabetes in humans. For this purpose, the insulin normally used is obtained from pigs, so-called "porcine insulin" or from cows, so-called "bovine insulin". It is also known that administration of either porcine insulin or bovine insulin, as normally available, often causes an antigenic response. In humans, this antigenic response can lead, over a prolonged period of dosing, to an increase in the daily dose required by the diabetic patient to control the disease.

It has now been discovered, and this is the basis of the present invention, that if porcine or bovine insulin, as normally available, is treated with a lysine specific amino-endopeptidase, that is a peptidase which cleaves a polypeptide at the peptide link attached to the amino group of lysine and does not require the lysine residue to be at the C-terminus of the peptide chain, then the products obtained are as potent as porcine or bovine insulin in causing a hypoglycaemic response, and furthermore, each of them causes a significantly smaller production of antibodies which bind insulin-like materials on subsequent administration than does the initial porcine or bovine insulin respectively. The enzyme removes the dipeptide L-lysyl-L-alanine from the C-terminus of the B chain of the porcine or bovine insulin, and the polypeptides so obtained have not been described previously.

According to the invention there is provided a polypeptide of the formula:

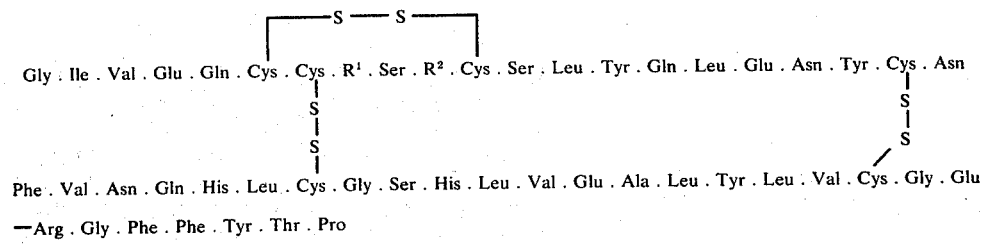

wherein either $R^1$ is threonine and $R^2$ is isoleucine, or $R^1$ is alanine and $R^2$ is valine.

The polypeptide wherein $R^1$ is threonine and $R^2$ is isoleucine differs from porcine insulin only in that the B chain, i.e. the longer chain, lacks the C-terminal lysyl and alanyl residues which form the 29th and 30th residues of the B chain of porcine insulin. This polypeptide can therefore be named des-Lys$^{29}$.Ala$^{30}$-porcine insulin, and this name will be used hereafter.

The polypeptide wherein $R^1$ is alanine and $R^2$ is valine differs from bovine insulin only in that the B chain lacks the C-terminal lysyl and alanyl residues. It can therefore be named as des-Lys$^{29}$-Ala$^{30}$-bovine insulin, and this name will be used hereafter.

According to a further feature of the invention, there is provided a process for the preparation of des-Lys$^{29}$-Ala$^{30}$-porcine insulin from porcine insulin or of des-Lys$^{29}$-Ala$^{30}$-bovine insulin from bovine insulin which comprises exposing the porcine or bovine insulin in an aqueous medium to the action of a lysine specific amino-endopeptidase followed by separation of the des-Lys$^{29}$-Ala$^{30}$-porcine insulin or des-Lys$^{29}$-Ala$^{30}$-bovine insulin from the remaining enzyme and lysyl-alanine.

As examples of suitable lysine specific amino-endopeptidases there may be mentioned the enzyme AM protease and the enzyme myxobacter AL-1 protease II.

The enzyme AM protease may be obtained from the mature fruiting bodies of the fungus *Armillaria mellea* as fully described and claimed in U.K. patent specification No. 1,263,956. The enzyme may also be obtained, slightly more conveniently, by a modification of the procedure described in U.K. Pat. No. 1,263,956 in which the chromatography step (iv) is carried out in two stages: firstly by adsorbing the crude enzyme on carboxymethyl cellulose at pH 4.5, and then eluting it with a pH 5.5 buffer and secondly by applying the concentrated eluate to the column described in step (iv) in the above patent.

The enzyme myxobacter Al-1 protease II may be obtained from *myxobacter* strain AL-1 as described by Wingard, Matsueda and Wolfe in the Journal of Bacteriology, Vol. 112, pages 940–949.

The exposure of the porcine or bovine insulin to the lysine specific amino-endopeptidase may be carried out with the enzyme simply dissolved in the aqueous medium, or it may be carried out with the enzyme bound to a support which may or may not be soluble in the aqueous medium.

The rate and extent of the reaction between the insulin used as starting material and the enzyme is dependent upon the enzyme/substrate ratio, the pH and temperature of the incubation medium, the concentration of insulin and the time of incubation. In general, of course, the time taken to cleave lysyl-alanine from the insulin used as starting material is shortened by an increase in either the concentration of the insulin or the enzyme/substrate ratio. Similarly, variation in the pH or temperature of the incubation medium affects the time needed to cleave the lysyl-alanine. The progress of the reaction may be monitored by examining samples of the reaction medium by either electrophoresis at pH 2.1 or separation on an automatic amino acid analyser, and so the desired end point of the reaction, that is essentially complete cleavage of lysyl-alanine, and the effect of any variation in the reaction conditions can readily be determined.

When the enzyme AM protease is used, the reaction will proceed at a wide variety of enzyme/substrate ratios, and indeed, as little as 1 part of enzyme to 10,000 parts of substrate can be used. The reaction will also proceed at a pH of the incubation medium from 3 to 10, and at a temperature from 10° C. to 60° C. With a given concentration of insulin, the reaction is fastest at a pH of from 4 to 9, but in the lower part of this pH range, the solubility of the insulin is relatively low so that a greater production of enzyme treated insulin is attainable at pH values in the higher part of the above range where the solubility of the insulin is greater. Accordingly, preferred reaction conditions to obtain essentially complete cleavage of lysyl-alanine in a relatively short period, for example 3–12 hours, are the use of a concentration of insulin near to its solubility in the incubation medium, a pH of from 7–9, a temperature of from 30° C. to 50° C. and as low an enzyme/substrate ratio as possible, for example 1/1,000 or less. It is also convenient to include metal ions in the incubation medium, for example calcium or magnesium in the form of their chlorides at a concentration $10^{-2}$ to $10^{-4}$ molar.

When the enzyme myxobacter Al-1 protease II is used, the reaction conditions are very similar to those which may be used with AM protease; an enzyme/substrate ratio as low as 1/10,000 may be used at a pH from 4 to 10 at a temperature from 25° C. to 5° C. Preferred conditions are the use of a concentration of insulin near to its solubility in the incubation medium, a pH of from 6 to 9, a temperature from 30° C. to 50° C., and as low an enzyme/substrate ratio as possible, for example 1/1,000 or less. Metal ions, for example calcium or magnesium may be included in the incubation medium.

As indicated above, the reaction may be carried out using the enzyme bound, preferably covalently, to a support. A variety of supports and methods of attachment are possible, and for details, a review by E. Katchalski in "Biochemical Aspects of Reactions on Solid Supports" ed. G. R. Stark, Academic Press 1971, should be consulted. One convenient method of attaching AM protease to a support is to activate agarose gel beads with cyanogen bromide, with or without spacer groups derived, for example, from hexylamine or hexanoic acid, and then allow the activated agarose to react with AM protease. Alternatively, the agarose gel beads may be activated using 2,4-dichloro-6-carboxymethylamino-s-triazine as coupling agent. Another useful alternative is the use of carboxymethyl cellulose hydrazide.

When the exposure to enzyme is carried out with the enzyme simply dissolved in the aqueous medium, the required des-Lys$^{29}$-Ala$^{30}$-porcine (or bovine) insulin may be separated from the other components of the incubation mixture by any cnventional technique for the separation of polypeptides, but the use of a molecular sieve technique is particularly convenient. Thus, the aqueous medium remaining after all the starting insulin has been degraded may be filtered through a column of cross-linked dextran gel or a polyacrylamide gel suitable for fractionating compounds of molecular weight 5,000–10,000 at any convenient pH, preferably removed from, and preferably substantially below, the isoelectric point of the polypeptides, and the column eluted with a buffer composed of components which are volatile on freeze drying under high vacuum, for example aqueous acetic acid, ammonium carbonate or ammonium acetate, to give the desired product which is isolated by freeze drying the eluate.

When the exposure to enzyme is carried out with the enzyme bound to support, separation of the required polypeptide from enzyme may be carried out by filtration in the normal way if the support is insoluble or using a filter for high polymers if the support is soluble in the aqueous medium.

As normally available, porcine or bovine insulin, even porcine or bovine insulin which has been crystallised several times, contains other polypeptides as impurities. These impurities are usually present in an amount being 3–5% by weight of the whole, and consist of materials such as pro-insulin, pro-insulin fragments and glucagon which can be difficult to separate from the insulin. Since some at least of these impurities, on exposure to a lysine specific amino-endopeptidase, are degraded to smaller polypeptides, incubation of porcine or bovine insulin with a lysine specific amino-endopeptidase and separation of the product obtained from the enzyme, lysyl-alanine and polypeptides of smaller molecular weight than insulin, i.e. oligopeptides, leads to a product containing a smaller proportion of impurities than did the starting preparation. Since it is conceivable that the impurities present in an insulin preparation contribute to its antigenicity, exposure of the insulin preparation to a lysine specific amino-endopeptidase can affect the antigenicity of the starting material by modifying the structure of the principal component and by reducing the amount of impurities.

Thus according to a slightly different aspect of the invention there is provided a process for the conversion of porcine or bovine insulin as normally available into a product having insulin-like activity but being less effective in causing the production of antibodies which bind insulin-like materials on subsequent administration than does the starting material, which comprises exposing the porcine or bovine insulin in an aqueous medium to the action of a lysine specific amino-endopeptidase and separating the material with insulin-like activity from the enzyme, lysyl-alanine and oligopeptides.

The incubation conditions and the isolation procedures are, of course, the same as described previously for the preparation of des-Lys$^{29}$-Ala$^{30}$-porcine insulin or des-Lys$^{29}$-Ala$^{30}$-bovine insulin.

As indicated above, the products and polypeptides of the invention have insulin-like activity and also cause a significantly smaller production of antibodies which bind insulin-like materials on subsequent administration than do the starting materials. The insulin-like activity is demonstrated by measuring the hypoglycaemic response produced by the products in rabbits using the technique set out in the United States Pharmacopeia, vol. 18, page 883. Equal weights of the products and the W.H.O. standard showed the same hypoglycaemic response within the accuracy of the method. The smaller production of antibodies is demonstrated by administering the test compounds, dissolved in a 50:50 mixture of complete Freund's adjuvant and saline, to rabbits, and then, one month later, measuring the insulin binding capacity of the rabbit's serum by adding a known amount of insulin labelled with I-125 to the serum and determining the amount of free and bound labelled insulin. This procedure is based on known methods, for example from Schlichtkrull et al. "Diabetes", vol. 21, Supplement 2, pages 649–656 (1972).

The new polypeptides of the invention are used for the management of diabetes in essentially the same way as porcine or bovine insulin. Thus they are administered parenterally, usually subcutaneously, either as a solution or as depot formulations having differing durations of action. Such formulations allow for a duration of action for up to 24 hours. Doses are selected for individual patients as required for the control of the diabetic and may be as high as 200 units daily.

As a further feature of the invention there is provided an injectable formulation comprising des-Lys$^{29}$-Ala$^{30}$-porcine insulin or des-Lys$^{29}$-Ala$^{30}$-bovine insulin as the essential active ingredient.

The invention is illustrated but not limited by the following Examples in which the terms 'Sephadex' and 'Sepharose' are trade marks:

EXAMPLE 1

Porcine insulin which had been re-crystallised 10 times (10 mg.) was dissolved in 0.1 M ammonium bicarbonate (1.0 ml.) and the solution incubated with AM protease (50 μg.) for 16 hours at 37° C.

One aliquot (10 μl.) of the incubation mixture was then analysed for N-terminal amino-acids by the well-known "dansylation" technique using 1-dimethylaminonaphthalene-5-sulphonyl chloride (Hartley, Biochem. J. 1970, 119, 805). Glycine (from insulin A chain), phenyl/alanine (from insulin B chain) and lysine (from lysyl-alanine) were found.

A second aliquot was examined by paper electrophoresis in acetic acid/formic acid at pH 2.1 (20 ml. formic acid, 80 ml. acetic acid made up to 1 liter with water) and showed H-Lys-Ala-OH, and another component (mobilities relative to ε-DNP-lysine 2.9 and 1.5 respectively). Elution of the second component and N-terminal amino-acid analysis revealed glycine and phenylalanine. Total amino-acid analysis gave integral amino-acid ratios of aspartic acid 3, serine 3, threonine 2, glutamic acid 7, proline 1, glycine 4, alanine 1, valine 4, isoleucine 2, leucine 6, phenylalanine 3, tyrosine 4, histidine 2, and arginine 1, together with cysteine in an amount which was not determined precisely. The compound thus differs from porcine insulin in having no lysine and only one residue of alanine.

A third aliquot was applied to the top of the resin column of a Locarte Amino-acid Analyser (Locarte Ltd., 24 Emperor's Gate, London S.W.7) and the (23 cm.) resin column eluted in the usual way at 55° C. with the programme, 90 min. (pH. 3.28), 55 min. (pH 4.25), 155 min. (pH 6.65) in which insulin appears after 234 minutes, Lys-Ala after 255 minutes, and des-Lys$^{29}$-Ala$^{30}$-porcine insulin after 223 minutes. Only two peaks corresponding to des-Lys$^{29}$-Ala$^{30}$-porcine insulin and Lys-Ala were detected.

The remainder of the incubation mixture was applied to a column (60 × 0.9 cm.) of porous cross-linked dextran gel ('Sephadex' G-50) equilibrated with 0.1 M ammonium carbonate. The column was developed with 0.1 M ammonium carbonate at a flow rate of 3 ml./hr. and fractions of 30 drops (1 ml.) were collected. The fractions were assayed for peptide material by measuring the U.V. absorption at 280 nm, and fractions 25–35 containing the main peak were combined and lyophilised to give des-Lys$^{29}$-Ala$^{30}$-porcine insulin.

EXAMPLE 2

Porcine insulin which had been crystallised 10 times was dissolved in 0.1 M ammonium bicarbonate containing calcium chloride to give a solution containing 2 mg. of insulin per ml. and a calcium chloride concentration of 3 × 10$^{-4}$ molar. Portions of this solution were then incubated at pH 8.2, 37° C. for 40 hours with amounts of AM protease giving the following enzyme/substrate ratios: 1/625, 1/1250, 1/2500 and 1/5000. Analysis of the incubation mixtures at intervals by the techniques described in Example 1 showed completed cleavage in each case apart from the 1/5000 reaction where 88% cleavage was obtained at the end of the experiment.

EXAMPLE 3

Porcine insulin which had been crystallised 10 times was dissolved in buffers prepared from ammonia and acetic acid of pH 4.0, 6.0, 8.0 and 10.0 containing calcium chloride to give 2 mg./ml. of insulin and 3 × 10$^{-4}$ molar calcium chloride. The solutions were incubated with AM protease at a 1/100 enzyme/substrate ratio at 37° C. for 6 hours. Analysis as in Example 2 showed that cleavage was taking place in each case.

EXAMPLE 4

Porcine insulin which had been crystallised 10 times was dissolved in 0.1 M ammonium bicarbonate buffer of pH 8.2 containing calcium chloride to give a solution containing 2 mg./ml. of insulin and 3 × 10$^{-4}$ molar calcium chloride. Portions of the solution were incubated with AM protease at an enzyme/substrate ratio of 1/1000 for 3 hours at temperatures of 23° C., 37° C., 45° C., and 55° C. Analysis as in Example 2 showed complete cleavage at 37° C. and 45° C., approximately 50% cleavage at 55° C. and a small amount of cleavage at 23° C.

EXAMPLE 5

A solution of porcine insulin [120 mg. - once crystallised porcine insulin purified by gel filtration (Sephadex G-50) in 0.1 M ammonium carbonate] in water (14 ml.), adjusted to pH 8.0 and containing 3 × 10$^{-4}$ M calcium chloride was incubated at 37° C. with AM protease (120 μg.) for 5 hours. During the incubation, the pH was kept at 8.0 by the automatic addition of 0.005 M sodium hydroxide solution. The resulting solution was applied to a column (100 × 1.4 cm.) of porous cross-linked dextran gel ('Sephadex' G-50) and the column developed with 0.1 M ammonium carbonate at a flow rate of 13 ml./hr. at 4° C. Fractions of 150 drops (5 ml.) were collected and assayed for peptide material by measuring their U.V. absorption at 280 nm. The fractions (22–30) containing the main peak were combined and lyophilised to give des-Lys$^{29}$-Ala$^{30}$-porcine insulin (100 mg.). On polyacrylamide gel electrophoresis at pH 8.9, this material appeared as a single component when stained with amido black. It had a mobility towards the anode of 1.2 relative to that of porcine insulin. It also gave the same integral amino-acid ratios as found in Example 1.

EXAMPLE 6

A solution of porcine insulin (1 mg.) in 0.1 M ammonium bicarbonate buffer of pH 8.2 (1 ml.) was applied to the top of a column (10 × 0.5 cm.) containing 3 ml. of 4% agarose gel beads on to which had been covalently bound 5 mg. of AM protease and equilibrated in the same ammonium bicarbonate buffer at 22° C. The column was eluted with ammonium bicarbonate buffer at a flow rate of 7 ml./hr. for 1 hour and the fractions assayed for peptide material by measuring the U.V. absorption at 280 nm. The fractions containing peptide material were combined and lyophilised to give des-Lys$^{29}$-Ala$^{30}$-porcine insulin having the same physical properties as the product of Example 5.

The agarose gel having AM protease bound to it was prepared as follows:

A suspension of 3 ml. of 4% agarose gel beads ('Sepharose' 4B) in 10 ml. of water was stirred with 450 mg. of cyanogen bromide for 20 minutes while the pH of the mixture was maintained at 10–11 by the addition of 4N sodium hydroxide. The suspension was then mixed with ice and washed with 2 l. of a cold pH 8.0 buffer solution containing sodium bicarbonate (0.1 M) and sodium chloride (1.0 M) in water. The washed suspension was then stirred with 13.5 ml. of a solution of AM protease (5 mg.) in the above pH 8.0 buffer at 4° C. for 12 hours. The solid was washed with 1 l. of the above pH 8.0 buffer, and then kept in a 1 M solution of ethanolamine at pH 8.0 for 2 hours. The solid was washed with (a) 0.1 M sodium acetate/acetic acid buffer of pH 4.0 containing 1.0 M sodium chloride and then (b) 0.1 M sodium borate buffer of pH 8.5 containing 1.0 M sodium chloride, and the washings with (a) and then (b) repeated four times. The agarose beads containing covalently bound enzyme were then equilibrated with 0.1 M ammonium bicarbonate of pH 8.2.

EXAMPLE 7

Solutions of porcine insulin (10 × crystallised) containing 1 mg./ml. were incubated at pH 8.0 and 40° C. for 2 hours with AM protease at an enzyme/substrate ratio of 1/1000 in the presence of magnesium chloride at concentrations of $10^{-1}$, $10^{-2}$, $10^{-3}$ and $10^{-4}$ molar respectively. Analysis as in Example 2 showed 90% cleavage with $10^{-1}$ molar Mg, 75% cleavage with $10^{-2}$ and $10^{-3}$ molar Mg. and 65% cleavage with $10^{-4}$ molar Mg. In the absence of magnesium, 68% cleavage took place.

EXAMPLE 8

A solution of crystalline bovine insulin (150 mg.) in water (2 ml.), adjusted to pH 8.3 and containing $10^{-2}$ M calcium chloride, was incubated with AM protease (140 μg.) for 3 hours at 37° C. During the incubation, the pH was kept at 8.3 by the automatic addition of 0.02 M sodium hydroxide solution. An aliquot of the solution (10 μl.) was examined using the amino-acid analyser as described in example 1, but with the programme 1 min. (pH 3.28), 1 min. (pH 4.25), 60 min. (pH 6.65) then the column regeneration cycle. The insulin peak (elution time 90 min.) was absent, whereas des-$Lys^{29}$-$Ala^{30}$-bovine insulin (elution time 80 min.) and Lys-Ala (elution time 120 min.) were both present. The incubated solution was then lyophilised, and the solid dissolved in M acetic acid (2 ml.). This solution was subjected to gel filtration at 4° C. as described in example 5 but with M acetic acid as solvent. The fractions comprising the main peak as measured by U.V. absorption at 280 nm. were combined and lyophilysed to give des-$Lys^{29}$-$Ala^{30}$-bovine insulin (113 mg.). On polyacrylamide gel electrophoresis (pH 8.9) this material appeared as a single component when stained with amido black. It had a mobility of 1.2 times that of bovine insulin towards the anode. Total amino-acid analysis gave the same integral amino-acid ratios as bovine insulin apart from there being no lysine and only two alanine residues. Only glycine and phenylalanine were detected as N-terminal amino-acids by the "dansylation" technique described in Example 1.

EXAMPLE 9

Once crystallised porcine insulin (150 mg.) was dissolved in water by the addition of N ammonium hydroxide, and the solution made up to 3.0 ml. with 0.1M ammonium bicarbonate. AM protease solution (150 μg., 0.5 ml.) was added, and the solution was kept at 37° C. for 11 hours. Analysis of an aliquot of the digest by the technique described in Example 8 showed that digestion was complete. The solution was diluted with 40% v/v aqueous acetic acid (3 ml.), and the resulting solution was applied to a column of 'Sephadex' G 50 (160 × 2.0 cm.). The column was eluted with 20% v/v aqueous acetic acid, and the eluate was monitored by measuring the U.V. absorption at 280 nm. Fractions of 300 drops were collected with the flow rate at 15 ml. per hour. The insulin peak appeared between fractions 45–56, these fractions were combined and dried to give des-$Lys^{29}$-$Ala^{30}$-porcine insulin (135 mg). Under these conditions AM protease labelled with I-125 appeared between fractions 36–43.

What we claim is:

1. An injectable formulation for producing a hypoglycaemic response comprising an effective amount of des-$Lys^{29}$-$Ala^{30}$-porcine insulin and a major amount of a pharmaceutically acceptable diluent or solvent.

2. An injectable formulation for producing a hypoglycaemic response comprising an effective amount of des-$Lys^{29}$-$Ala^{30}$-bovine insulin and a major amount of a pharmaceutically acceptable diluent or solvent.

3. An injectable formulation for producing a hypoglycaemic response comprising an effective amount of the product obtained by exposing porcine insulin as normally available in an aqueous medium to the action of a lysine specific amino-endopeptidase and then separating the material with insulin-like activity from the enzyme, lysyl-alanine and oligopeptides formed by cleavage of impurities present in the porcine insulin as normally available, and a major amount of a pharmaceutically acceptable diluent or solvent.

4. An injectable formulation for producing a hypoglycaemic response comprising an effective amount of the product obtained by exposing bovine insulin as normally available in an aqueous medium to the action of a lysine specific amino-endopeptidase and then separating the material with insulin-like activity from the enzyme, lysyl-alanine and oligopeptides formed by cleavage of impurities present in the bovine insulin as normally available, and a major amount of a pharmaceutically acceptable diluent or solvent.

5. A method of producing a hypoglycaemic response in a host requiring such treatment while at the same time causing a smaller production of antibodies which bind insulin-like materials on subsequent administration than does porcine insulin as normally available, comprising administering an effective amount of des-$Lys^{29}$-$Ala^{30}$-porcine insulin or the product obtained by exposing porcine insulin as normally available in an aqueous medium to the action of a lysine specific amino-endopeptidase and then separating the material with insulin-like activity from the enzyme, lysyl-alanine and oligopeptides formed by cleavage of impurities present in the porcine insulin as normally available.

6. A method of producing a hypoglycaemic response in a host requiring such treatment while at the same time causing a smaller production of antibodies which bind insulin-like materials on subsequent administration than does bovine insulin as normally available, comprising administering an effective amount of des-$Lys^{29}$-$Ala^{30}$-bovine insulin or the product obtained by exposing bovine insulin as normally available in an aqueous medium to the action of a lysine specific amino-endopeptidase and then separating the material with insulin-like activity from the enzyme, lysyl-alanine and oligopeptides formed by cleavage of impurities present in the bovine insulin as normally available.

* * * * *

UNITED STATES PATENT OFFICE
CERTIFICATE OF CORRECTION

Patent No. 3,989,821      Dated November 2, 1976

Inventor(s) Harold GREGORY and Peter Leslie WALTON

It is certified that error appears in the above-identified patent and that said Letters Patent are hereby corrected as shown below:

In Item [30], Foreign Application Priority Data

"Dec. 18, 1972" should read --Dec. 28, 1972--

Signed and Sealed this

Twenty-second Day of February 1977

[SEAL]

Attest:

RUTH C. MASON
*Attesting Officer*

C. MARSHALL DANN
*Commissioner of Patents and Trademarks*